United States Patent [19]
McAleer et al.

[11] Patent Number: 5,989,917
[45] Date of Patent: *Nov. 23, 1999

[54] GLUCOSE MONITOR AND TEST STRIP CONTAINERS FOR USE IN SAME

[75] Inventors: Jerome F. McAleer, Wantage, United Kingdom; Piet H. C. Moerman, Zemst, Belgium; Ta Siu, Alhambra, Calif.

[73] Assignee: Selfcare, Inc., Waltham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/600,449

[22] Filed: Feb. 13, 1996

[51] Int. Cl.$^6$ .............................. G01N 1/00; G01N 33/50
[52] U.S. Cl. ................... 436/46; 436/50; 422/50; 422/61; 422/67; 422/68.1; 422/104
[58] Field of Search .................. 422/50, 55, 58, 422/61, 67, 99, 102, 104, 68.1; 436/44, 46, 50

[56] References Cited

U.S. PATENT DOCUMENTS

| | | | |
|---|---|---|---|
| 3,770,382 | 11/1973 | Carter et al. | 422/67 |
| 4,225,410 | 9/1980 | Pace | 204/195 R |
| 4,303,887 | 12/1981 | Hill et al. | 324/441 |
| 4,413,407 | 11/1983 | Columbus | 29/825 |
| 4,578,716 | 3/1986 | Van Rijckevorsel et al. | 360/1 |
| 4,592,893 | 6/1986 | Poppe et al. | 422/56 |
| 4,751,184 | 6/1988 | Higo et al. | 435/287 |
| 4,852,025 | 7/1989 | Herpichbohm | 364/551.01 |
| 4,900,424 | 2/1990 | Birth et al. | 204/409 |
| 4,963,245 | 10/1990 | Weetall | 204/403 |
| 5,000,180 | 3/1991 | Kuypers et al. | 128/635 |
| 5,053,199 | 10/1991 | Keiser et al. | 422/68.1 |
| 5,108,564 | 4/1992 | Szuminsky et al. | 204/153.12 |
| 5,120,420 | 6/1992 | Nankai et al. | 204/403 |
| 5,126,034 | 6/1992 | Carter et al. | 204/403 |
| 5,264,106 | 11/1993 | McAleer et al. | 204/403 |
| 5,277,870 | 1/1994 | Fuller et al. | 422/82.05 |
| 5,281,395 | 1/1994 | Markart et al. | 422/82.05 |
| 5,286,362 | 2/1994 | Hoenes et al. | 204/403 |
| 5,288,636 | 2/1994 | Pollmann et al. | 435/288 |
| 5,366,609 | 11/1994 | White et al. | 204/403 |
| 5,437,999 | 8/1995 | Diebold et al. | 435/288 |
| 5,489,414 | 2/1996 | Schreiber et al. | 422/64 |
| 5,505,308 | 4/1996 | Eikmeier et al. | 206/449 |
| 5,507,288 | 4/1996 | Böcker et al. | 128/633 |
| 5,575,403 | 11/1996 | Charlton et al. | 221/31 |

FOREIGN PATENT DOCUMENTS

| | | |
|---|---|---|
| 0170375 | 2/1986 | European Pat. Off. . |
| 0351892 | 1/1990 | European Pat. Off. . |
| 0359891 | 3/1990 | European Pat. Off. . |
| 0555654 | 8/1993 | European Pat. Off. . |
| 0567067 | 10/1993 | European Pat. Off. . |
| 677149 | 4/1991 | Switzerland . |
| 89/08713 | 9/1989 | WIPO . |
| 9410558 | 5/1994 | WIPO . |

OTHER PUBLICATIONS

Book of DS199x Touch Memory Standard, Dallas Semiconductor 1990.

Primary Examiner—Long V. Le
Attorney, Agent, or Firm—Oppedahl & Larson LLP

[57] ABSTRACT

A test meter of the type which receives a disposable test strip and a sample of bodily fluid from a patient and performs an electrochemical analysis of the amount of an analyte such as glucose in the sample includes a receptacle for receiving a container in which disposable test strips are provided, and a mechanism for reading information about the disposable test strips that is affixed to the container. For example, calibration values can be applied to the container in the form of a machine readable bar-code, a magnetic stripe, a memory chip or as a resonant wire loop. By automatically obtaining calibration values from the container in which the strips are provided, the chances of using the wrong calibration information are greatly reduced. The container may also contain information readable by the meter including the expiration date, and the number of test strips in the container.

36 Claims, 6 Drawing Sheets

5,989,917

GLUCOSE MONITOR AND TEST STRIP CONTAINERS FOR USE IN SAME

BACKGROUND OF THE INVENTION

This application relates to an improved type of glucose monitor which is automatically calibrated for the particular test strips being used, and to test strip containers for use in such a monitor.

Glucose monitoring is a fact of everyday life for diabetic individuals, and the accuracy of such monitoring can literally mean the difference between life and death. To accommodate a normal life style to the need for frequent monitoring of glucose levels, a number of glucose meters are now available which permit the individual to test the glucose level in a small amount of blood. The success of these devices, however, depends on the ability of the user to obtain a correct reading.

Many of the meter designs currently available make use of a disposable test strip which in combination with the meter measures the amount of glucose in the blood sample electrochemically. Lot-to-lot variation during the manufacture of test strips requires that the user calibrate the system for each batch of strips. This is normally accomplished by inserting a calibration strip, provided with each package of test strips, into the meter. This process introduces the possibility of error as a result of failure of the user to perform the calibration procedures in the correct manner or at the correct times. In particular, errors in calibration can occur if a user opens a new package of test strips and fails to perform the calibration step or if a user has several packages of test strips open and confuses the calibration strips between the packages.

It is an object of the present invention to provide a meter, and particularly a glucose meter, which obviates the need for user initiated calibration.

It is a further object of the invention to provide a meter, and particularly a glucose meter, which reduces the likelihood of a test strip being used with the incorrect meter calibration.

SUMMARY OF THE INVENTION

These and other objects of the invention are provided by a test meter of the type which receives a disposable test strip and a sample of bodily fluid from a patient and performs an electrochemical analysis of the amount of an analyte, for example glucose, in the sample that includes a receptacle for receiving a container in which disposable test strips are provided, and a mechanism for reading calibration values calibration values specific to the disposable test strips that are affixed to the container. For example, calibration values can be applied to the container in the form of a machine readable bar-code, a magnetic stripe, a memory chip or as a resonant wire loop. By automatically obtaining calibration values from the container in which the strips are provided, the chances of using the wrong calibration information are greatly reduced.

In addition to calibration values, the container may contain additional information readable by the meter which will enhance the safety of the individual using the device. For example, the container may include a machine readable expiration date, which would permit the meter to either give a warning or to refuse to process a test strip which was beyond its expiration date. In addition, the container may include information about the number of test strips in the container. Since any effort to process more strips than were originally supplied in the container would in all likelihood result in the use of the wrong calibration codes, a warning or refusal to process the strip would be appropriate in this instance as well.

DETAILED DESCRIPTION OF THE INVENTION

Figure 1:
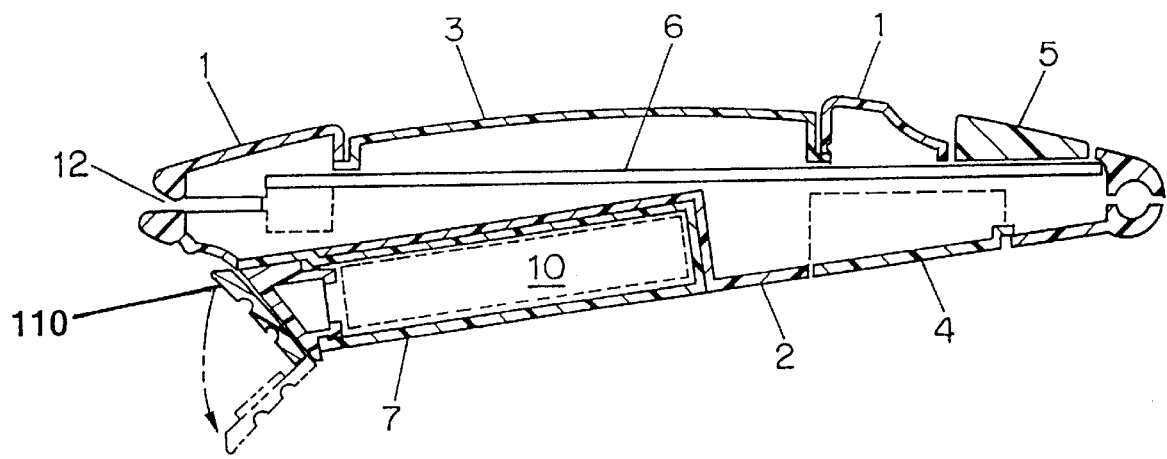
FIG. 1 shows a cross section of a glucose meter in accordance with the invention.
Figure 2:
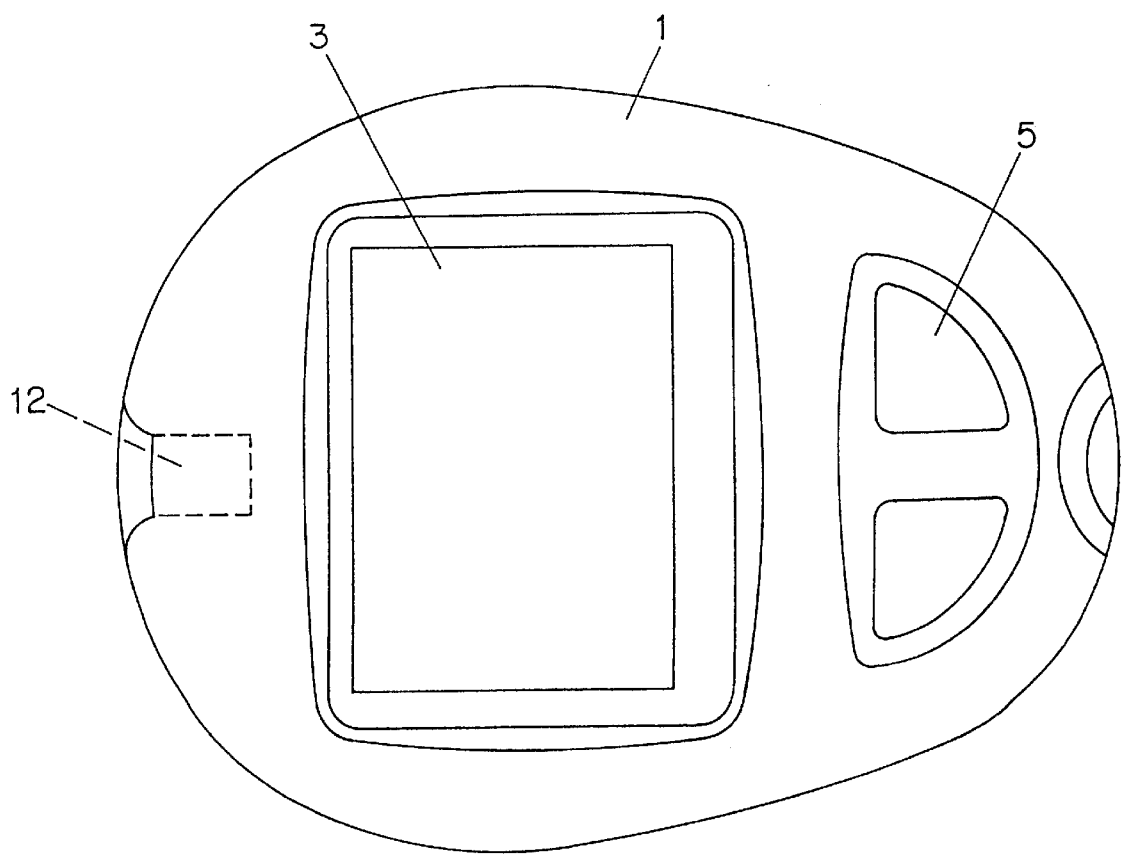
FIG. 2 shows a top view of a glucose meter in accordance with the invention.

FIGS. 1 and 2 shows a meter in accordance with the invention. The meter has a top housing member 1 and a bottom housing member 2. Bottom housing member 2 has a receptacle 7 affixed thereto for receiving a container 10 of test strips. Bottom housing member 2 also has an opening for receiving batteries to power the meter which is sealed in use by battery cover 4. Top housing member 1 has openings formed therein for a liquid crystal or light emitting diode display 3, and for control buttons 5. In addition, top housing member 1 and bottom housing member 2 taken together form a slot 12 into which a test strip is inserted for measurement of glucose. As shown, the slot 12 forms a connection between the exterior of the housing and an interior region in which electronics for measuring the amount of analyte are disposed.

As shown in FIG. 1, the receptacle 7 has an open end providing access to the receptacle from the exterior of the housing and through which the container 10 is received. At the inner end, the receptacle does not provide an operative connection for disposable test strips to the interior region of the housing,. Thus, when the test meter of the invention is in use, a test strip is removed from a container 10 disposed within the receptacle 7 through opened container lid 110 and inserted into slot 12.

Figure 3:
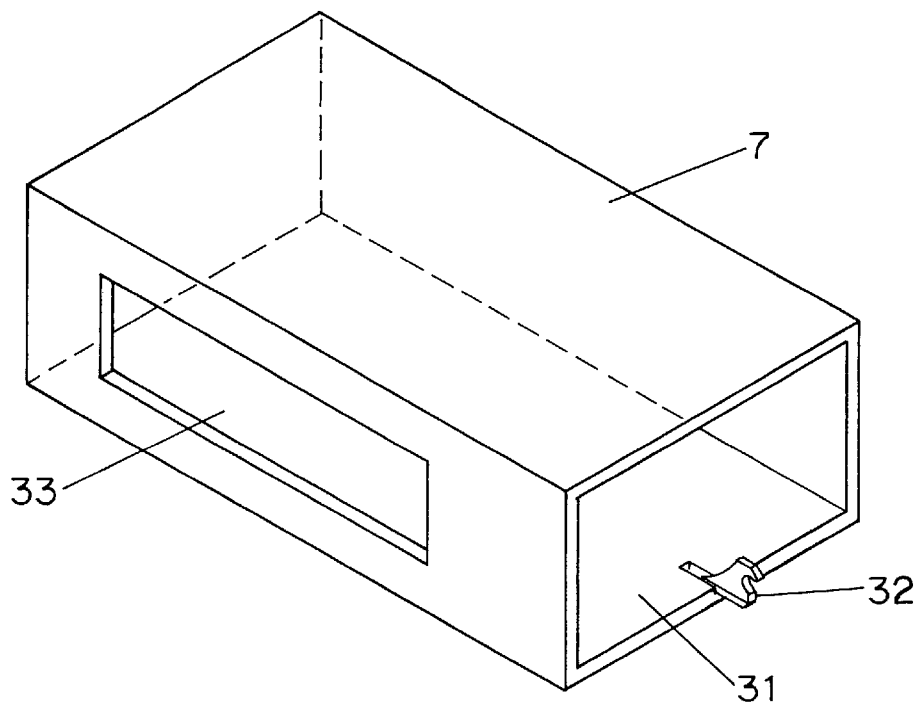
FIG. 3 shows one embodiment of a receptacle for receiving a container of test strips in accordance with the invention.

FIG. 3 shows a detailed view of one embodiment of a receptacle for a test strip container in accordance with the present invention. The receptacle 7 is open at the front end 31 to receive a test strip container and has a retractable catch 32 for holding the container in position in the receptacle. On one surface of the receptacle 7 is an opening 33 through which machine-readable characters, e.g. a bar code, printed on the container can be read. Although the receptacle 7 in FIG. 3 is shown as a regular shape, it may be desirable to make the container and the receptacle of corresponding asymmetrical shapes to ensure alignment of the machine-readable characters with the opening.

Figure 4:
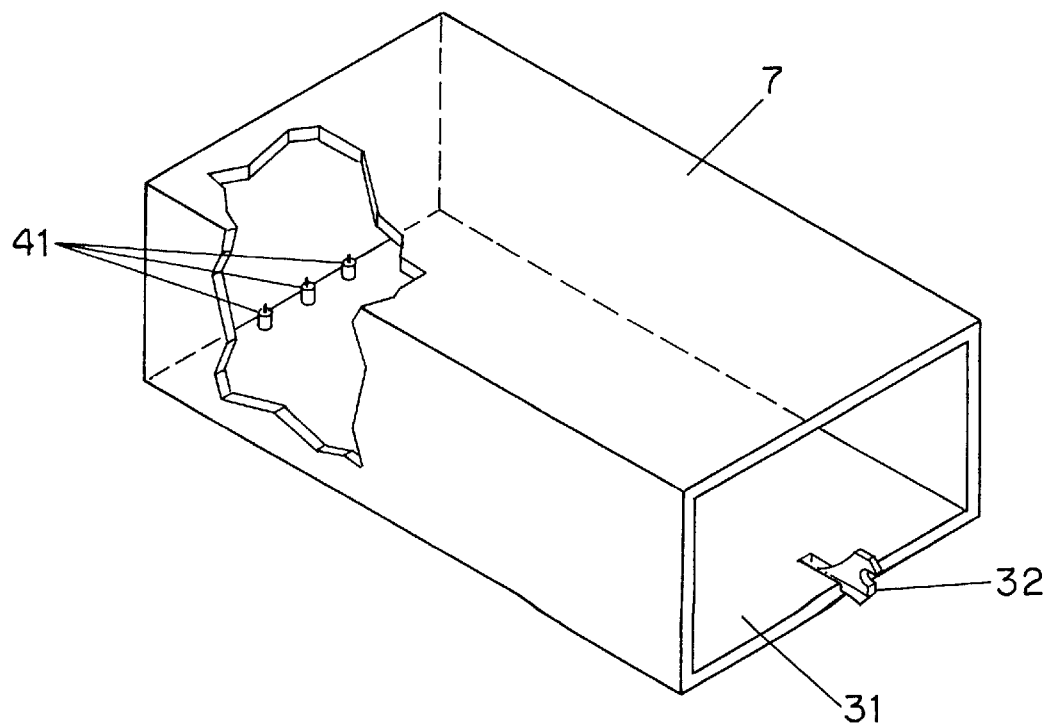
FIG. 4 shows one embodiment of a receptacle for receiving a container of test strips in accordance with the invention.

FIG. 4 shows a cross section of an alternative embodiment of the receptacle 7, In this embodiment, a line of electrical contacts 41 are arranged to engage with a corresponding set of contacts on the container to that information stored on a chip built into the container can be made. The contacts 41 are in turn connected to the meter for processing of the information.

Figure 5:
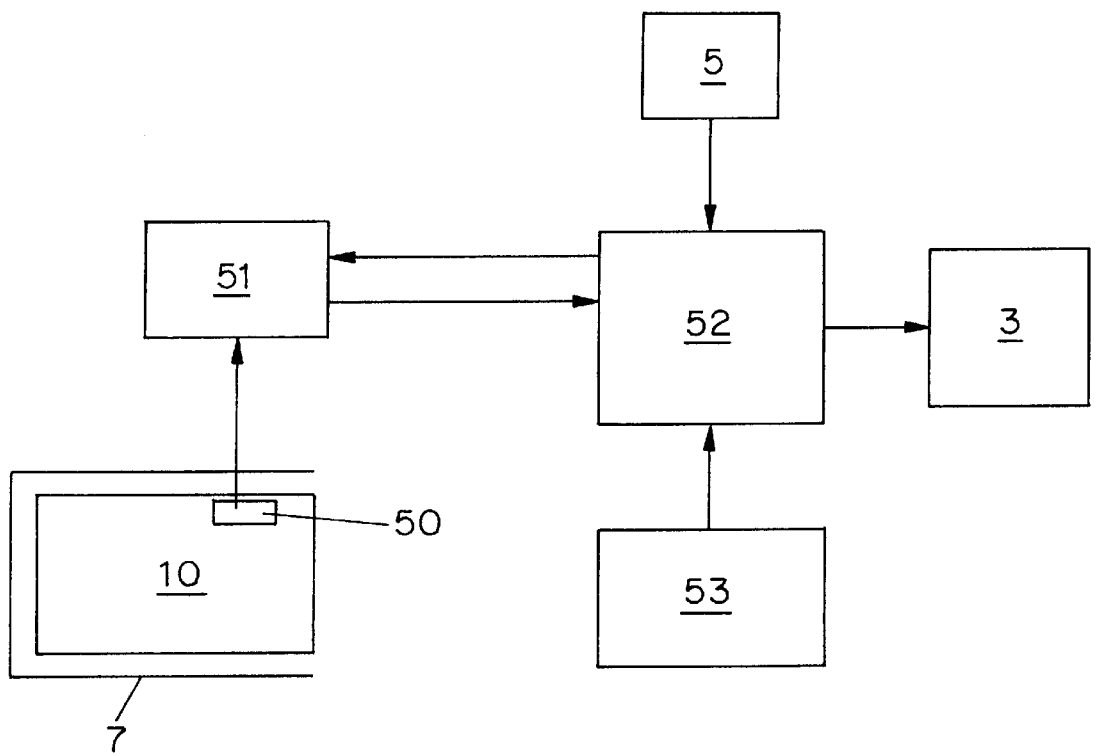
FIG. 5 shows the functional parts of a meter in accordance with the invention schematically.

FIG. 5 shows functional parts of the glucose meter of the invention schematically for purposes of understanding the operation of the invention. As shown, coded information 50 recorded on a test strip container 10 disposed within receptacle 7 is functionally connected to means 51 for reading the information affixed to the container. The means for reading the information must, of course, be compatible with the manner in which the information 50 is recorded on the container. Thus, for example, in the case of information recorded in a bar-code format, the means 51 for reading the information affixed to the container will be a bar-code reader. For a magnetic strip, the means 51 will be a magnetic stripe reader. In the case where the information on the container is recorded in a memory chip, for example a "TOUCH MEMORY" chip manufactured by Dallas Semiconductor or other semiconductor device capable of storing information for retrieval by a remote device, the means 51 for reading the information is a microprocessor which sends a query to the chip and receives back a signal reflecting the stored contents of the chip. In the case where the information is stored as a resonating wire loop, the resonating frequency of which indicates the information, the means 51 for reading the information is an rf generator and detector which scans across possible resonance frequencies and monitors for a resonant emission from the wire loop.

The means 51 for reading the information is functionally connected to a microprocessor 52 for controlling the device. When the user depresses the start key 5, the microprocessor 52 queries the means 51 for reading the information from the container and either evaluates the sample which has placed in the slot 12, evaluates the sample with a warning to the user, or refuses to evaluate the sample. If the sample is evaluated, with or without a warning, the microprocessor receives output from the electrodes 53 on the test strip, applies the calibration factors received from the means 51 for reading the information from the container, and causes the resulting glucose level to be displayed on display 3.

FIGS. 6 A–E illustrate several variations of information 50 which can be recorded on a container in accordance with the present invention, and the ways in which the microprocessor 52 can make use of the recorded information. In FIG. 6A, the information 50 recorded on the container is simply the calibration values for the test strips in the container. In this case, the microprocessor 52 simply applies the calibration values to the raw electrode output and converts it to a digital value, to arrive at a calibrated glucose display.

Figure 6A:
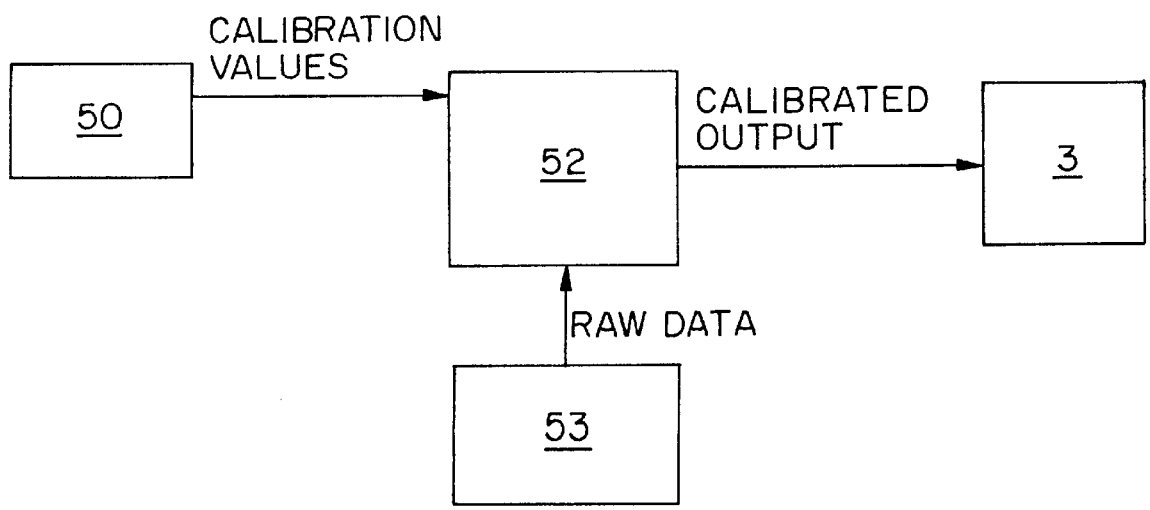
FIGS. 6A–6E illustrate the operation of several embodiments of the inventions.
Figure 6B:
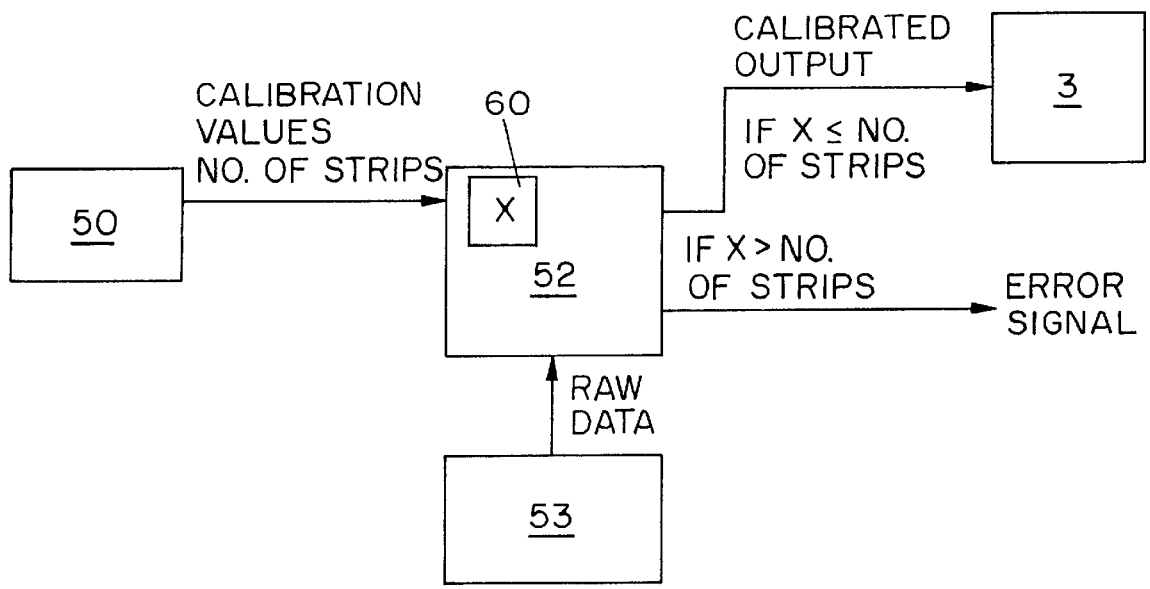

In FIG. 6B, the information 50 recorded on the container includes both the calibration values and the number of test strips originally in the container. Micro-processor 52 maintains a register 60 in which a counter X is stored. The counter X is set to zero whenever a new container is loaded into the receptacle 7, and is incremented each time a test strip is evaluated. Each time the meter is used, the microprocessor 52 compares the value of X stored in register 60 to the number of test strips originally in the container. If the X is less than or equal to the original number of test strips, the microprocessor operates in a normal manner and a calibrated glucose value is displayed. If X is greater than the original number of strips, the microprocessor generates an error signal. This error signal may cause the meter to provide a result together with a warning that the result is suspect, or may cause the microprocessor to refuse to display a result at all.

Figure 6C:
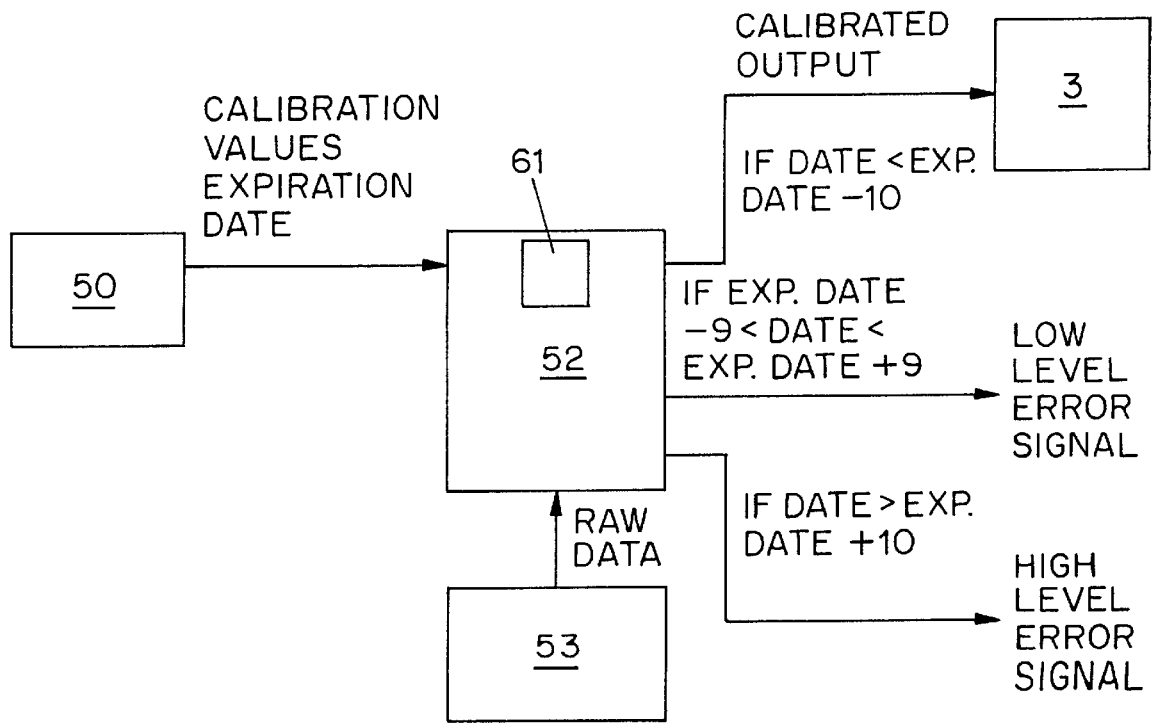

FIG. 6C shows an embodiment in which the information 50 recorded on the container includes calibration values and an expiration or manufacturing date. In this case, the microprocessor 52 includes a clock 61 which is set initially by the user or by the factory and which is incremented automatically by the microprocessor to maintain the date accurately. The microprocessor 52 compares the expiration date recorded on the container to the clock, and acts in one of three ways depending on the results of this comparison. As shown, when the actual date is before the expiration date by some pre-determined threshold amount, for example 10 days, the microprocessor 52 simply generates a calibrated glucose display. When the actual date is closer to the expiration date than the predetermined threshold, and perhaps for several days after the expiration date, the microprocessor 52 generates a low level error signal which causes the meter to display a calibrated glucose reading along with a warning. Thereafter, the microprocessor generates a high level error signal which results in the meter refusing to provide a reading.

Figure 6D:
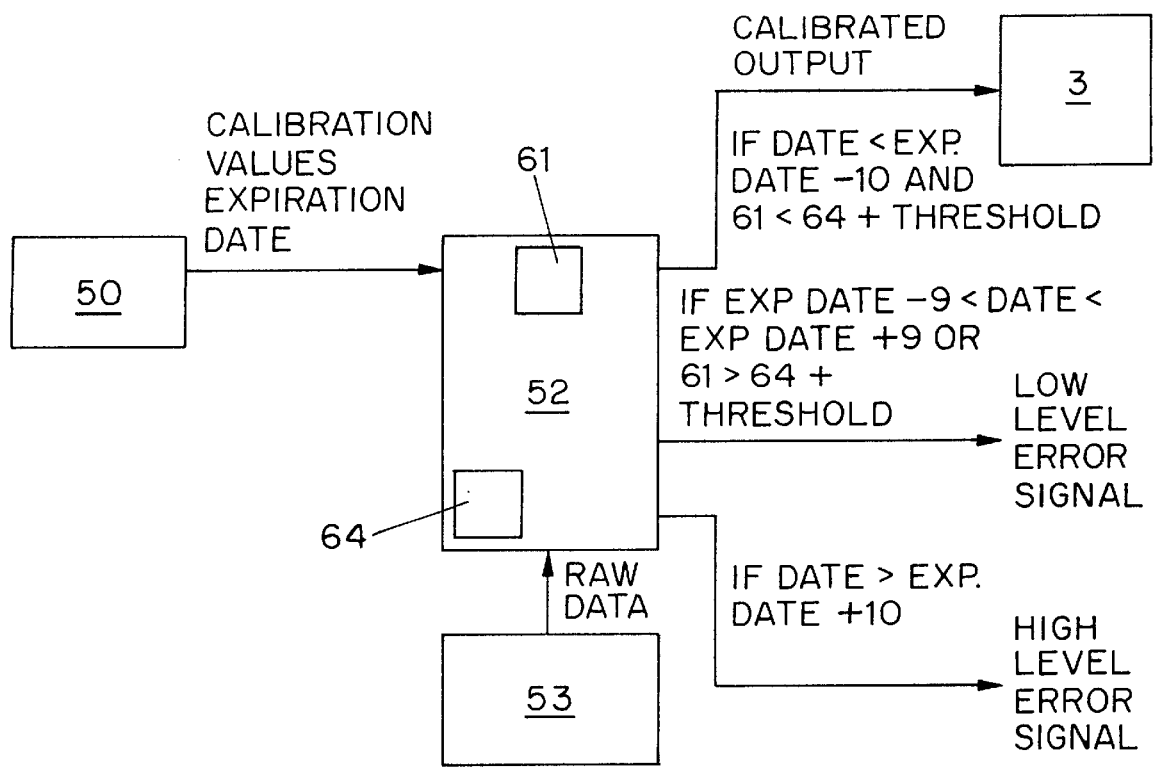

A variation on the embodiment shown in FIG. 6C would use the clock to also monitor the time since the container was placed in the receptacle. In this case, as shown in FIG. 6D, the microprocessor would also include a storage register 64 in which the date on which a new container is placed in the receptacle is stored. In addition to checking the expiration date, the microprocessor 52 would also compare the current date to the date stored in register 62. If this difference were greater than a predetermined threshold level, the meter would generate a warning and/or refuse to operate. This embodiment is particularly useful where the shelf life of the test strips in the sealed container is longer than the shelf life after the container has been opened for first use. In addition, by generating a warning when a container of strips is lasting longer than expected, the meter could provide a reminder that tests need to be performed on a regular basis.

Figure 6E:
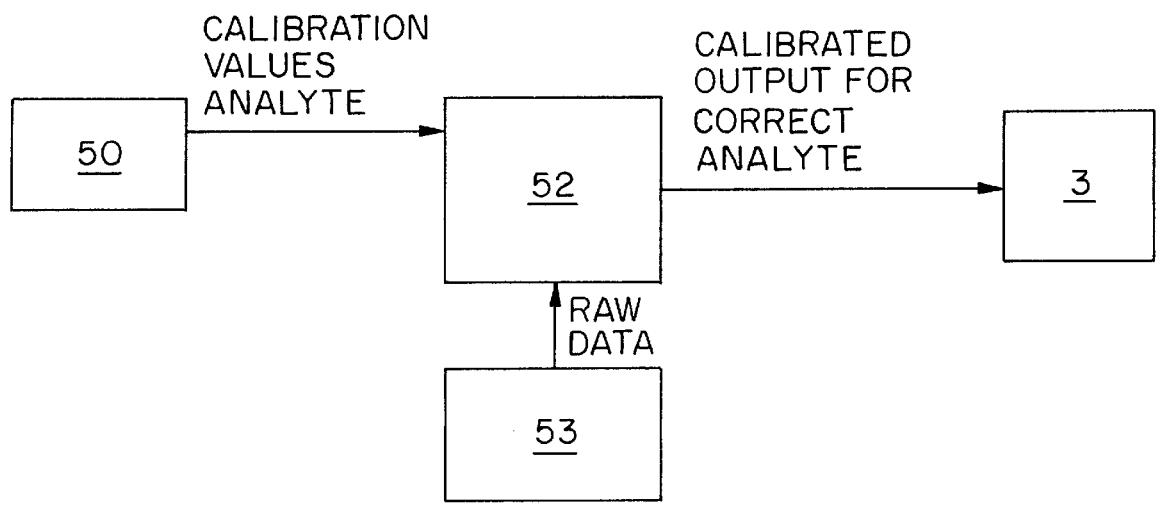

FIG. 6E shows a further embodiment of the invention in which the information 50 stored on the container includes both calibration values and the identification of the analyte for which the strip is intended. This embodiment is particularly useful where disposable test strips for several analytes, for example glucose and ketones can be evaluated in the same meter but require different processing of the raw data to obtain optimum results.

The various types of information and the resulting processing options depicted in the FIGS. 6A–6E can be used in any combination. Thus, for example, a container in accordance with the invention might include calibration values, analyte ID and expiration date; calibration values, number of strips and expiration date; number of strips and expiration date; or any other combination of information types.

While the checks described above will greatly reduce the chances of using incorrect calibration values or out-of-date test strips, it may also be advantageous to provide the ability to deactivate the information stored on the container so that it cannot be used beyond a certain point. For example, deactivation of the container after a number of tests had been run equal to the number of strips into the container would eliminate the possibility that an individual might place additional test strips which did not match the calibration values of the container.

The mechanism of deactivation, like the mechanism for reading the information depends on the manner in which the information is stored. For example, in the case of a bar-code, the information might be rendered unreadable by exposing a photosensitive region to light which causes a color change for example to alter the bar code to an unreadable pattern. For an emitter loop, a fusible link can be included which is fused by a pulse of an appropriate frequency, render the shorting the emitter loop and rendering it inoperative. In the case of a programmable memory chip, deactivation might be accomplished by writing over a portion of the stored information, or by inducing a magnetic field near the chip of sufficient magnitude to render the stored information meaningless, and therefore unreadable. The generation of a magnetic field will also render a magnetic stripe inoperative.

Figure 7:
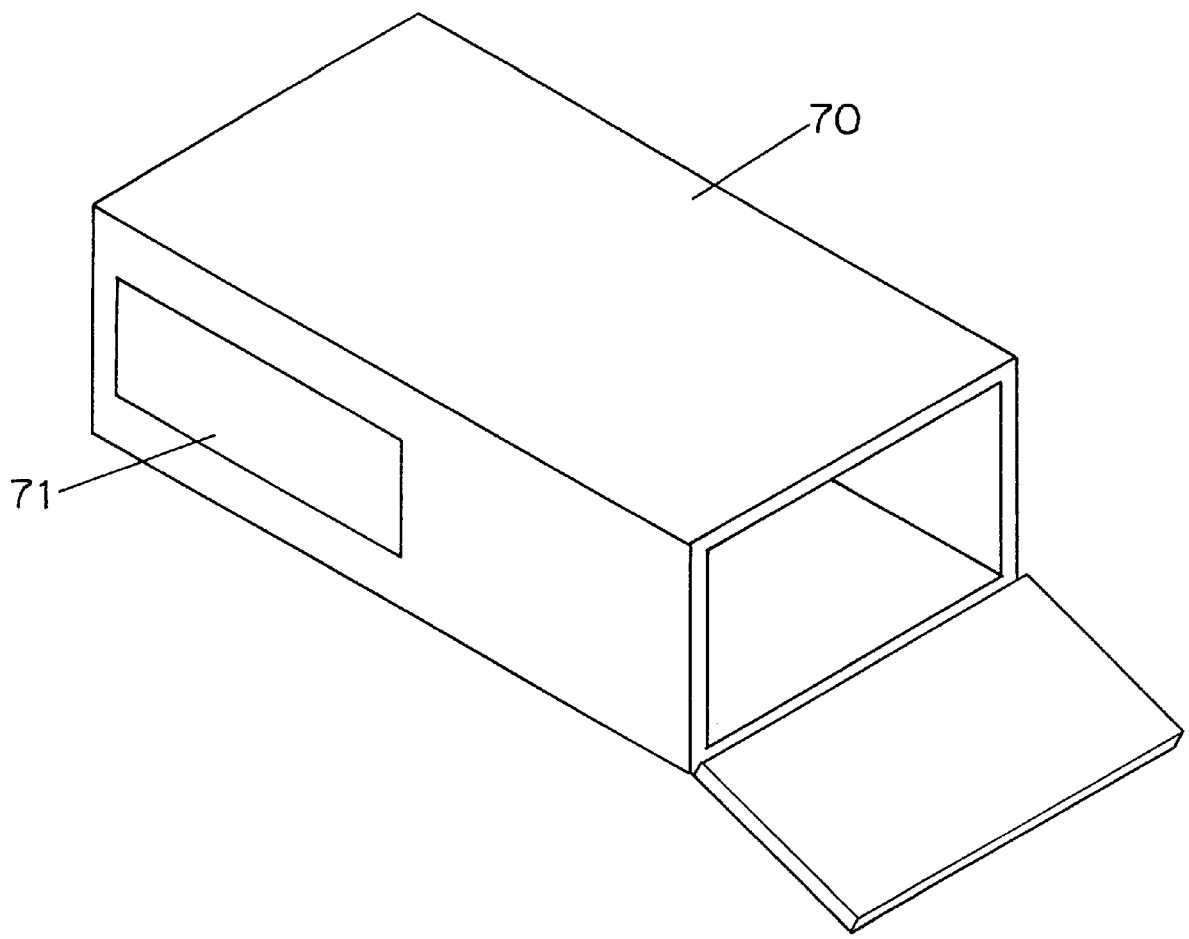
FIG. 7 shows a container in accordance with the invention.

A further aspect of the present invention is the containers which can be used in the meter according to the invention. As shown in FIG. 7, such a container generally comprises a sealable body member 70 for receiving at least one glucose test strip; and machine-readable means 71 for storing information specific to disposable test strips provided in the container. As will be apparent from the foregoing discussion of the alternative reading means which can be included in a meter according to the invention, the machine readable means 71 can be a bar-code, a memory chip, or a resonant wire loop, or any other form of machine readable storage which can be adapted for use in a small device of the type claimed.

We claim:

1. A test meter which receives a disposable test strip and a sample of bodily fluid from a patient and performs an electrochemical analysis of the amount of an analyte in the sample, comprising
   (a) a housing having formed therein
      a slot for receiving a disposable test strip with a sample of bodily fluid thereon, said slot forming a connection between the exterior of the housing and an interior region in which electronics for measuring the amount of analyte are disposed; and
      a receptacle for receiving a container in which disposable test strips are provided, said receptacle having an open end providing access to the receptacle from the exterior of the housing and through which the container is received, and an inner end which does not provide an operative connection for disposable test strips to the interior region of the housing, said container having affixed thereto information specific to the disposable test strips provided in the container in a form readable by the test meter;
   (b) means for reading the information affixed to the container while it is in the receptacle.

2. The test meter according to claim 1, wherein the means for reading the information comprises a bar-code reader.

3. The test meter according to claim 1, wherein the means for reading the information comprises a radio frequency emitter and receiver effective to evaluate a resonant wire loop used to store information specific to the test strips in the container.

4. The test meter according to claim 1, wherein the means for reading the information comprises a microprocessor for retrieving information from a memory chip used to store information specific to the test strips in the container.

5. The meter according to claim 1, wherein the information specific to the disposable test strip includes calibration values for the disposable test strips, and wherein the meter further comprises means for applying the calibration values to a raw data value to produce a calibrated value for the amount of analyte.

6. The meter according to claim 5, further comprising means for displaying the calibrated value for the amount of analyte.

7. The meter according to claim 1, wherein the information specific to the disposable test strip includes the number of test strips originally provided in the container, and the meter further comprises a data storage register for storing a value equal to the number of test strips used from the container and means for generating an error signal whenever the value stored in the data storage register exceed the number of test strips originally provided in the container.

8. The meter according to claim 7, wherein the information specific to the disposable test strip includes calibration values for the disposable test strips, and wherein the meter further comprises means for applying the calibration values to a raw data value to produce a calibrated value for the amount of analyte.

9. The meter according to claim 1, wherein the information specific to the disposable test strip includes the expiration date of test strips provided in the container, and the meter further comprises a data storage register for storing the current date and means for generating an error signal whenever the value stored in the data storage register is later than the expiration date of the test strips provided in the container.

10. The meter according to claim 9, wherein the means for generating an error signal generates a low level error signal which causes the meter to display a calibrated result and a warning when the date stored in the data register is within some predetermined number of days before or after the expiration date, and a high level error signal which causes the meter to refuse to display a calibrated result when the date stored in the data register is more than the predetermined number of days after the expiration date.

11. The meter according to claim 9, wherein the information specific to the disposable test strip includes calibration values for the disposable test strips, and wherein the meter further comprises means for applying the calibration values to a raw data value to produce a calibrated value for the amount of analyte.

12. The meter according to claim 1, further comprising means for rendering the information affixed to the container unreadable when a predetermined set of conditions is met.

13. The meter according to claim 1, wherein the analyte is glucose.

14. The test meter according to claim 13, wherein the means for reading the information comprises a bar-code reader.

15. The test meter according to claim 13, wherein the means for reading the information comprises a radio frequency emitter and receiver effective to evaluate a resonant wire loop used to store information specific to the test strips in the container.

16. The test meter according to claim 13, wherein the means for reading the information comprises a microprocessor for retrieving information from a memory chip used to store information specific to the test strips in the container.

17. The meter according to claim 13, wherein the information specific to the disposable test strip includes calibration values for the disposable test strips, and wherein the meter further comprises means for applying the calibration values to a raw data value to produce a calibrated value for the amount of analyte.

18. The meter according to claim 17, further comprising means for displaying the calibrated value for the amount of analyte.

19. The meter according to claim 13, wherein the information specific to the disposable test strip includes the number of test strips originally provided in the container, and the meter further comprises a data storage register for storing a value equal to the number of test strips used from the container and means for generating an error signal whenever the value stored in the data storage register exceed the number of test strips originally provided in the container.

20. The meter according to claim 19, wherein the information specific to the disposable test strip includes calibration values for the disposable test strips, and wherein the meter further comprises means for applying the calibration values to a raw data value to produce a calibrated value for the amount of analyte.

21. The meter according to claim 13, wherein the information specific to the disposable test strip includes the expiration date of test strips provided in the container, and the meter further comprises a data storage register for storing the current date and means for generating an error signal whenever the value stored in the data storage register is later than the expiration date of the test strips provided in the container.

22. The meter according to claim 21, wherein the means for generating an error signal generates a low level error signal which causes the meter to display a calibrated result and a warning when the date stored in the data register is within some predetermined number of days before or after the expiration date, and a high level error signal which causes the meter to refuse to display a calibrated result when the date stored in the data register is more than the predetermined number of days after the expiration date.

23. The meter according to claim 21, wherein the information specific to the disposable test strip includes calibration values for the disposable test strips, and wherein the meter further comprises means for applying the calibration values to a raw data value to produce a calibrated value for the amount of analyte.

24. The meter according to claim 13, further comprising means for rendering the information affixed to the container unreadable when a predetermined set of conditions is met.

25. A system for the detection of glucose comprising,
a test meter which receives a disposable test strip and a sample of bodily fluid from a patient and performs an electrochemical analysis of the amount of an analyte in the sample, said meter comprising:
(a) a housing having formed therein
slot for receiving a disposable test strip with a sample of bodily fluid thereon, said slot forming a connection between the exterior of the housing and an interior region in which electronics for measuring the amount of analyte are disposed; and
a receptacle for receiving a container in which disposable test strips are provided, said receptacle having an open end providing access to the receptacle from the exterior of the housing and through which the container is received, and an inner end which does not provide an operative connection for disposable test strips to the interior region of the housing, said container having affixed thereto information specific to the disposable test strips provided in the container in a form readable by the test meter;
(b) means for reading the information affixed to the container while it is in the receptacle, and
a container of disposable glucose test strips sized to be placed within the receptacle, said container comprising:
(a) a sealable body member for receiving at least one glucose test strip;
(b) machine-readable means for storing information specific to glucose test strips provided in the container; and
(c) at least one disposable glucose test strip for electrochemical analysis of the amount of the glucose in a sample disposed within the sealable body member.

26. The system according to claim 25, wherein the machine-readable means is a bar-code.

27. The system according to claim 25, wherein the machine-readable means is a memory chip.

28. The system according to claim 25, wherein the machine-readable means is a resonant wire loop.

29. The according to claim 25, wherein the machine-readable means is a magnetic stripe.

30. The system according to claim 25, further comprising means for rendering the machine-readable means unreadable in response to an externally applied signal.

31. The system according to claim 25, wherein the information specific to the test strips includes calibration values for the test strips.

32. The system according to claim 31, wherein the information specific to the test strips includes the number of test strips originally provided in the container.

33. The system according to claim 31, wherein the information specific to the test strips includes the expiration date of the test strips provided in the container.

34. The system according to claim 25, wherein the information specific to the test strips includes the number of test strips originally provided in the container.

35. The system according to claim 25, wherein the information specific to the test strips includes the expiration date of the test strips provided in the container.

36. A method for detection of glucose in a sample of bodily fluid from a patient comprising the steps of:
providing an analytical system comprising:
a test meter which receives a disposable glucose test strip and a sample of bodily fluid from a patient and performs an electrochemical analysis of the amount of glucose in the sample, said meter comprising:
(a) a housing having formed therein
a slot for receiving a disposable glucose test strip with a sample of bodily fluid thereon, said slot forming a connection between the exterior of the housing and an interior region in which electronics for measuring the amount of glucose are disposed; and
a receptacle for receiving a container in which disposable glucose test strips are provided, said receptacle having an open end providing access to the receptacle from the exterior of the housing and through which the container is received, and an inner end which does not provide an operative connection for disposable test strips to the interior region of the housing, said container having affixed thereto information specific to the disposable test strips provided in the container in a form readable by the test meter;
(b) means for reading the information affixed to the container while it is in the receptacle, and
a container of disposable glucose test strips disposed within the receptacle, said container comprising
(a) a sealable body member for receiving at least one disposable glucose test strip;
(b) machine-readable means for storing information specific to glucose test strips provided in the container; and
(c) at least one disposable glucose test strip for electrochemical analysis of the amount of the glucose in a sample disposed within the sealable body member;
removing a test strip from the container disposed within the receptacle; inserting the removed test strip into the slot formed in the housing; and applying the sample to the test strip.

* * * * *